(12) United States Patent
Luquet

(10) Patent No.: US 6,607,905 B1
(45) Date of Patent: Aug. 19, 2003

(54) **LACTIC FERMENT COMPRISING A PARTICULAR STRAIN OF *LACTOBACILLUS ACIDOPHILUS* AND USE THEREOF**

(75) Inventor: François-Marie Luquet, Orsay (FR)

(73) Assignee: Bio-K + International Inc., Laval (CA)

( * ) Notice: Subject to any disclaimer, the term of this patent is extended or adjusted under 35 U.S.C. 154(b) by 0 days.

(21) Appl. No.: 09/322,030

(22) Filed: May 28, 1999

Related U.S. Application Data

(63) Continuation of application No. PCT/CA97/00915, filed on Nov. 28, 1997.
(60) Provisional application No. 60/032,157, filed on Nov. 29, 1996.

(51) Int. Cl.$^7$ .............................. C12N 1/20; C12N 1/00; A01N 63/00; A23C 9/123
(52) U.S. Cl. ................. 435/252.9; 435/854; 424/934.5; 424/93.3; 426/34
(58) Field of Search .............................. 435/252.9, 854; 424/93.45, 93.3; 426/34

(56) References Cited

U.S. PATENT DOCUMENTS

| | | | |
|---|---|---|---|
| 5,516,684 A | | 5/1996 | Saito et al. ............... 435/252.9 |
| 5,716,615 A | * | 2/1998 | Cavaliere Vesely et al. ........................ 424/93.4 |

FOREIGN PATENT DOCUMENTS

| | | |
|---|---|---|
| EP | 0181170 | 11/1985 |
| EP | 0199535 | 4/1986 |
| EP | 0577903 | 1/1994 |
| EP | 0577904 | 1/1994 |
| GB | 2261372 | 5/1993 |

OTHER PUBLICATIONS

Inhibiton of Shigella sonnei by *Lactobacillus casei* and *Lact. acidophilus*; Marie E. Nader et al. Journal of Applied Bacteriology 1992, vol. 73 pp. 407–411.

Mital et al. Critical Review in Microbiology 1995, 21(3), pp. 175–214.

Gonzalez et al. Microbiology—Aliments—Nutrition. 1990, vol. 8, pp. 349–354.

* cited by examiner

*Primary Examiner*—Irene Marx
*Assistant Examiner*—Vera Afremova
(74) *Attorney, Agent, or Firm*—Robic

(57) ABSTRACT

The purified strain of *Lactobacillus acidophilus* CNCM/I-1492 (*L.a.* 1492) when administered alone or in combination with another *Lactobacillus acidophilus* (*L.a.*) strain and *Lactobacillus casei* (*L.c.*) strain, has a beneficial effect on the cholesterol blood level in mammals. It also strenghtens the immune system, facilitates the absorption of nutrients and stimulates the intestinal flora. Such strains also neutralize side effects caused by antibiotics. The invention concerns the specific strain *L.a.* I-1492, a ferment comprising *L.a.* I-1492, *L.a.* and *L.c.* strains, a dairy product obtained by this ferment and a method of manufacturing the dairy product.

5 Claims, No Drawings

LACTIC FERMENT COMPRISING A PARTICULAR STRAIN OF *LACTOBACILLUS ACIDOPHILUS* AND USE THEREOF

This application is a continuation application of International Application Number PCT/CA97/00915, filed Nov. 28, 1997, which in turn claims priority to U.S. Provisional Application No. 60/032,157, filed Nov. 29, 1996, both of which are incorporated herein by reference.

FIELD OF THE INVENTION

The present invention concerns a purified strain *Lactobacillus acidophilus* identified as CNCM/I-1492 (hereinafter called *L.a.* I-1492), the microorganism from this strain, a lactic ferment comprising this strain, a process for making dairy products using this ferment, and the dairy products obtained by this process and containing at least 500 million per gram of *Lactobacillus acidophilus* (including the *L.a.* I-1492 strain) or 380 million/gram of *L.a.* I-1492.

The invention also concerns the use of a ferment comprising the strain *Lactobacillus acidophilus* CNCM/I-1492 and of a dairy product containing the same in the pharmaceutical field for reducing the level of cholesterol in the blood of a mammal.

BACKGROUND

Yogurts are fermented dairy products obtained by fermentation of different lactic bacterias with milk. The most widely used milk is cow's milk. These lactic bacterias (mainly *Streptococcus thermophilus* and *Lactobacillus bulgaricus*) are foreign bodies to the human intestinal flora and are not implanted in the digestive system during consumption of these dairy products.

Other lactic bacterias are present in their natural state in the human digestive system. It seems that the presence of such bacterias are beneficial and helpful in particular to improve the absorption of food while maintaining the equilibrium in the intestinal flora. Such other bacterias in particular are *Lactobacillus casei* and *Lactobacillus acidophilus*.

The dairy products containing such bacterias are of particular interest inasmuch as they allow better digestion and provide an easier absorption of calcium when the latter is in the presence of moderate amounts of lactose. Indeed, during fermentation, milk protein and sugar are hydrolyzed, thereby facilitating hydrolisation of minerals such as calcium, iron essential to their absorption.

It has also been demonstrated that the ingestion of a fermented milk containing *Lb Acidophilus* alone increase the phagocytes activities thereby stimulating non specific defense of the host.

Furthermore, the consumption of fermented milk *Lb casei* and milk *Lb acidophilus* has been found effective to rapidly reduce acute diarrhea in humans. *Lb acidophilus* has also been found to have a healing effect on other gastric-intestinal related problems such as diverticulitis, food poisoning, abnormal fermentation.

However, perfecting such products is extremely difficult inasmuch as these bacterias naturally present in humans are not easily given to rapid production of dairy products having a pleasant taste and texture.

Furthermore, it is known that the performance of combined strains in a same ferment is unpredictable because of the interactions between the strains. Hence the performance and properties of a ferment can be significantly different from the performance and properties of the pure strains of which the ferment is composed.

It has now been, surprisingly, discovered that the *Lactobacillus acidophilus* I-1492 strain, or *L.a.* I-1492, has not only a beneficial effect on digestion and the equilibrium of the intestinal tract, but also has a major pharmaceutical effect allowing the reduction of the cholesterol level in the blood of mammals, and more particularly humans.

This effect is particularly remarkable when the strain *L.a.* I-1492 is combined with some lactic bacterias in a lactic ferment. A thorough study of these products has revealed, in a totally surprising and unexpected way, that fermented dairy products obtained from such ferment display therapeutic properties which reduce the amount of cholesterol in the blood. The main factor seems to evidently be due to the presence of a high concentration of the strain *L.a.* I-1492 since such an effect has not been established for other yogurts and/or lactic bacterias. The combination of lactic bacterias which compose the ferment according to the invention, allows an increase and acceleration of the development of the strain *L.a.* I-1492 during production of the fermented dairy product. Furthermore, it is very likely that this ferment creates a synergy and thereby achieves the production of a fermented dairy product having improved therapeutic results as compared to the dairy products obtained with the *L.a.* I-1492 strain alone.

BRIEF DESCRIPTION OF THE INVENTION

The present Invention concerns a purified strain *Lactobacillus acidophilus* I-1492 (*L.a.* I-1492) and the microorganism from this strain.

This strain can used in a lactic ferment, which is also an object of the invention, comprising a mixture of the following lactic strains:

*L.a.* I-1492 at least one other *Lactobacillus acidophilus* strain; and at least one *Lactobacillus casei* strain.

The latter two strains may be of commercial origin and can be purchased from manufacturers of lactic ferments. For example, the commercial *Lactobacillus acidophilus* strain that is used in the ferment of the present invention may be the one sold under the trademark RP Texel by Rhône-Poulenc or the one sold under the trademark *L.a.* RO-52 by Rosell. The commercial *Lactobacillus casei* strain may be the one sold under the trademark E2AL by Rhône-Poulenc.

Another object of the invention is a fermented lactic product of the yogurt type obtained by fermentation of the strain or of the lactic ferment according to the invention, with a dairy compound.

A further object of the invention is a method of manufacturing a fermented dairy product by the fermentation of the ferment according to the invention, said product having the texture of a yogurt.

A further object of the invention is the use of such fermented dairy product in the stimulation of the immune system for curing sore throat, flu, sinusitis and urinary infection. This same fermented dairy product has also been found to be useful in treating gastric-intestinal related diseases and infections.

Still a further object of the invention is the use of the above dairy products to reduce the cholesterol blood level in mammals, especially humans, and a method of medical treatment comprising the ingestion of a dairy product according to the invention.

The invention as well as its advantages will be better understood upon reading the following non-restrictive description, and by referring to the enclosed drawings.

DETAILED DESCRIPTION OF THE INVENTION

The purified *Lactobacillus acidophilus* strain I-1492 according to the invention was filed on Nov. 15, 1994 in the National Collection of Microorganism Cultures (25, Rue du Dr. ROUX, F-75724 Paris Cedex 15) according to the provisions of the Budapest Treaty.

The physiological, chemical and biochemical characteristics of the *acidophilus* strains that may be used in the ferment according to the invention are shown in tables 1 and 2. It has been found that the *L.a.* I-1492 strain present chemical, biochemical and physiological characteristics similar to those of the other *L.a.* strains. As a matter of fact, the *L.a.* I-1492 strain differs from the others only in that it degrades cholesterol more efficiently.

TABLE 1

Lactobacillus type (Group I): physiological characteristics

| Species | Mobility | Growth at/in 15° C. | Growth at/in 45° C. | pH 3.3 | pH 0.7 | 4% NaCl | 10% NaCl | Optimal Growth temperature | Maximum Growth temperature |
|---|---|---|---|---|---|---|---|---|---|
| L.b. acetotolerans | – | – | – | – | + | – | | | <40° C. |
| L.b. acidophilus | – | – | – | + | – | + | | 45° C. | 52° C. |
| L.b. amylophilus | – | – | + | | | | | 30° C. | <45° C. |

TABLE 2

Lactobacillus type (Group I): chemical and biochemical characteristics

| Species | G & C % | Type of Murein | Nature of the teichoic acid | lactic acid isomer | electrophoretic mobility of L-LDH | D-LDH | LDH ALLOSTERIC | ARGININE DEHYDROLASE | GAS FROM D-GLUCOSE | GAS FROM D-GLUCOSATE |
|---|---|---|---|---|---|---|---|---|---|---|
| L.b acetotolerens | 35–36 | Lys D-Asp | | DL | | | | – | – | – |
| L.b. acidophilus | 34–37 | Lys D-Asp | Glycerol | DL | 1.35–1.5 | 1.3 | – | – | – | – |

The fermenting profile for the *L.a.* strains which include the *L.a.* I-1492 strain is shown in table 3.

TABLE 3

Lactobacillus type (Group I): fermenting profile

ACID FERMENTATION FROM:

| SPECIES | ESCULIN HYDROLYSIS | ADONITOL | STARCH | AMYODALINE | ARABINOSE | CELLOBIOSE | FRUCTOSE | GALACTOSE |
|---|---|---|---|---|---|---|---|---|
| Lb acetotolerens group I | ± | – | – | – | – | – | + | – |
| Lb acetotolerens group II | + | – | – | – | – | + | + | – |
| Lb acidophilus | + | v | + | – | + | v | + | + |

ACID FERMENTATION FROM:

| SPECIES | GLUCONATE | GLUCOSE | GLYCEROL | INOSITOL | INULIN | LACTOSE | MALTOSE |
|---|---|---|---|---|---|---|---|
| Lb acetotolerens group I | – | + | | | | – | + |
| Lb acetotolerens group II | – | + | | | | – | v |
| Lb acidophilus | – | + | | | | + | + |

ACID FERMENTATION FROM:

| SPECIES | ESCULIN HYDROLYSIS | MANNITOL | MANNOSE | MELEZITOSE | MELIBIOSE | RAFFINOSE | RHAMNOSE | RIBOSE |
|---|---|---|---|---|---|---|---|---|
| Lb acetotolerens group I | ± | + | + | – | – | – | – | + |
| Lb acetotolerens group II | + | – | + | – | – | – | – | – |
| Lb acidophilus | + | – | + | – | v | v | – | – |

TABLE 3-continued

Lactobacillus type (Group I): fermenting profile

| | ACID FERMENTATION FROM: | | | | | | |
|---|---|---|---|---|---|---|---|
| SPECIES | SACCHAROSE | SALICIN | SORBITOL | L-SORBOSE | TREHALOSE | XYLOSE | DEXTRINS |
| Lb acetotolerens group I | − | + | − | − | + | − | |
| Lb acetotolerens group II | − | + | − | − | + | − | |
| Lb acidophilus | + | + | − | − | v | − | − |

The chemical, biochemical and physiological characteristics of the *casei* strain which can be used in the ferment according to the invention in combination with the *L.a.* I-1492 strain, are compiled in tables 4 and 5.

TABLE 4

Lactobacillus type (Group II) Chemical and biochemical characteristics

| | | | | | | | Production of: | | |
|---|---|---|---|---|---|---|---|---|---|
| | | NATURE OF | LACTIC | electrophoretic | | | ARGININE | GAS FROM | GAS FROM |
| | TYPE | TEICHOIC | ACID | mobility of | | LDH | DEHYDRO- | D- | D- |
| Species | G & C % | OF MUREIN | ACID | ISOMER | L-LDH | D-LDH | ALLOSTERIC | GENASE | GLUCOSE | GLUCOSATE |
| Lb.casel | 45–47 | Lys D-Asp | — | L(+) | 1.22 | 0.93 | + | − | | |

TABLE 5

Lactobacillus type (Group II): physiological characteristics

| | | growth at/in: | | | | | | Optimal | Maximum |
|---|---|---|---|---|---|---|---|---|---|
| Species | Mobility | 15° C. | 45° C. | pH3.3 | pH7.0 | 6.5% NaCl | 10% NaCl | Growth temperature | Growth temperature |
| Lb.casel | − | | + | v | | | | 30 & 37° C. | <45° C. |

The fermenting profile of the casei strain is shown in table 6.

TABLE 6

Lactobacillus type (Group II): fermenting profile

| | Acid Production by fermentation of: | | | | | | | |
|---|---|---|---|---|---|---|---|---|
| Species | ESCULIN HYDROLYSIS | N-ACE-TYL GLUCOSAMINE | ADONITOL | STARCH | AMYODALINE | ARABINOSE | D-ARABITOL | L-ARABITOL |
| Lb.casel | + | | − | − | + | − | | |

| Species | ARBUTIN | CELLOBIOSE | 2-CÉTO-GLUCONATE | 5-CÉTO-GLUCONATE | DEXTRINS | DULCITOL | ERYTHRITOL |
|---|---|---|---|---|---|---|---|
| Lb.casel | + | + | | | v | − | |

| | ACID PRODUCTION BY FERMENTATION OF: | | | | | | |
|---|---|---|---|---|---|---|---|
| Species | ESCULIN HYDROLYSIS | D-FUCOSE | L-FUCOSE | FRUCTOSE | GALACTOSE | GENTIOBIOSE | GLUCONATE | GLUCOSE | GLYCEROL |
| Lb.casel | + | − | v | + | + | − | + | + | − |

| | ACID PRODUCTION BY FERMENTATION OF: | | | | | | |
|---|---|---|---|---|---|---|---|
| Species | GLYCOGEN | INOSITOL | IMULIE | LACTOSE | D-LYSCOSE | MALTOSE | MANNITOL | MANNOSE |
| Lb.casel | − | − | − | − | | | v | + |

TABLE 6-continued

Lactobacillus type (Group II): fermenting profile

| Species | ESCULIN HYDROLYSIS | MELEZITOSE | MELIBIOSE | α-METHYL-D-GLUCOSIDE | α-METHYL-D-MANNOSIDE | β-METHYL-XYLOSIDE | RAFFINOSE | RHAMNOSE | RIBOSE |
|---|---|---|---|---|---|---|---|---|---|
| Lb.casel | + | + | | − | | | | − | |

| Species | SACCHAROSE | SALICIN | SORBITOL | L-SORBOSE | D-TAGATOSE | THREALOSE | D-TURANOSE | XYLITOL | XYLOSE |
|---|---|---|---|---|---|---|---|---|---|
| Lb.casel | − | + | − | − | | | + | − | |

A dairy product according to the present invention can be obtained by fermenting the ferment of the invention in a milk-based medium. For this purpose, the following process may be used.

Firstly, the L.a. I-1492, acidophilus and casei strains are incubated in a MRS type fermentation medium under 10% of $CO_2$ according to a standard program comprising several steps. The recombined lacteal base which is partially lactose-free and degassed is pasteurized for 1,5 minutes at 95° C. and inoculated at 10%. Finally, it is incubated according to the following program:

1) the L.a. I-1492 strain: 2 hours at 37° C. under 10% $CO_2$;
2) the acidophilus strain: 2 hours at 37° C.; and
3) the casei strain: 1 hour at 37° C.

The product is then co-fermented in an anaerobic atmosphere and medium for 15 hours at 37° C. (degassing under $CO_2$).

In order to realize the invention, any acidophilus and casei strains may be used as long as they present no health risk. Preferably, the following acidophilus strain should be used: RP Texel™ by Rhône-Poulenc and L.a. RO-52™ by Rosell. The commercial casei E2AL™ by Rhône-Poulenc is preferably used. The proportions of L.a. I-1492, acidophilus and casei cultured strains, are respectively about 70/20/10. These proportions may evidently be somewhat varied. Nevertheless, the total concentration of Lactobacilli acidophilus (including those obtained from L.a. I-1492 strains) which is present in the dairy product once fermented, must be at least equal to $500*10^6$/g and the concentration of L.a. I-1492 must be at least $380*10^6$/g.

Although total amino acid content is similar to milk, free amino acid are significantly higher. The level of peptides comprised in the fermented dairy product, having a molecular weight between 1000 and 5000 Da. is around 30% and the level of small peptides having less than 10 residues is approximately 15%. It is known that such levels of peptides fortify, in a surprising way, the immune and digestive systems.

In the fermented dairy product thus obtained, the dairy proteins are disintegrated into peptides whose size may be more or less large, allowing for an easier digestion of the product. Indeed, subject allergic to milk proteins were able to digest the fermented dairy product thus obtained. Once the fermented dairy product is manufactured, it is thereafter refrigerated and must be consumed before it deteriorates. Generally, the consumption of the same must take place within a period of 60 to 120 days.

A dairy product according to the invention has been commercialized by the applicant, Bio-K PLUS International Inc. (whose address is: 635 Victoria, Westmount, H3Y 2R9, CANADA) since Jun. 2, 1996, under the trade-mark Bio K+. However, the ferment of the present invention, which comprises the L.a. I-1492, acidophilus and casei strains has never been disclosed. Nor have the specific purified strain L.a. I-1492 and method of manufacturing the commercialized Bio K + product been disclosed. As it may be appreciated, a man skilled in the art would not, with the commercialized Bio K+ product at hand, be able to reproduce the same product.

The applicant has also suprisingly found that the fermented dairy product according to the invention has a stimulation effect on the immune system and is thereby effective for treating various inflammatory reactions and/or infectious diseases such as colds, sinusitis, urinary infections. The recommended treatment is a dose of 100 g per day of the fermented dairy product for a period of 10 to 60 days depending on the case. Furthermore the fermented dairy product neutralizes side effects caused by antibiotics.

The fermented dairy product of the invention has also been found to have significant effect in treating diseases and infections related to the intestinal tract such as diarrhea, diverticulitis, mega-colon, Crohn disease. Indeed, the applicant has found that daily consumption of the dairy product of the invention eliminates most cases of the above-mentioned diseases.

Furthermore, the fermented dairy product of the present invention contains a fair amount of folic acid and vitamin B12 which was produced during fermentation of the lactic culture. As a result, consumption of such product resulted in fast recuperation time in subjects whom regularly exercise. This observation is especially true for older individuals. As a matter of fact, 8 out of 10 people consuming the product on a daily basis said they felt better.

The fermented dairy product according to the invention may also be used for the treatment of high blood levels of cholesterol. The recommended treatment consists of a dose of 100 g per day for a period of 30 to 60 days.

The effect of this dairy product on the level of cholesterol in the blood was tested on a group of 14 patients to whom was prescribed a dose of 100 g per day for a period of, depending on the case, 30 to-60 days. The results of these tests are shown in the following charts where the total cholesterol blood level (CHO total) present in the blood is indicated. Hence, these tests reveal that upon regular intake during a period of 60 days, the total cholesterol level failed from between 7 to 22% and that the "low density level" (LDL) failed from between 9 to 25%. Furthermore, the level of triglycerides (TRIGLY) drops from between 28 to 43%. It can be seen that after 60 days of treatment, certain individuals recover a normal level of CHO/HDL (High density level) ratio, that is, a level comprised between 3.2 to 4.4 or of LDL/HDL ratio (that is, inferior to 3.8 for people aged 30 and over).

Of course, the above-mentioned example is solely for the purpose of illustrating the invention and is given only as a representative means. It must not be used to limit the scope of the invention which may extend to any obvious variations. For example, one may consider administering the ferment of the invention or powder on a dehydrated support.

| BIOK + CHOLESTEROL STUDY | | | | |
|---|---|---|---|---|
| | T = 0 | T = 30 | T = 60 | T = 120 REDUCTION |
| RD Case #1 (Med) | | | | |
| CHO TOTAL | 6,64 | 6,06 | 5,16 | 22% after 60 days |
| HDL | 0,72 | 0,62 | 0,66 | |
| LDL | not available | | | |
| TRIGLY | 4,64 | 6,64 | 4,59 | |
| CHO/HDL | 9,22 | 9,77 | 7,82 | |
| LDL/HDL | not available | | | |
| RM Case #2 (Med) | | | | |
| CHO TOTAL | 5,90 | 5,05 | 4,65 | 21% after 60 days |
| HDL | 1,36 | 1,44 | 1,14 | |
| LDL | 4,13 | 3,25 | 3,09 | 25% after 60 days |
| TRIGLY | 0,91 | 0,80 | 0,93 | |
| CHO/HDL | 4,33 | 4,43 | 4,07 | |
| LDL/HDL | 3 | 2,3 | 2,7 | |
| EC Case #3 (Med) | | | | |
| CHO TOTAL | 7,94 | 6,49 | | 18% after 30 days |
| HDL | 0,98 | 0,84 | | |
| LDL | 5,86 | 4,88 | | 17% after 30 days |
| TRIGLY | 2,41 | 1,70 | | 29% after 30 days |
| CHO/HDL | 8,10 | 7,72 | | |
| LDL/HDL | 6 | 5,8 | | |
| MB Case #4 (Med) | | | | |
| CHO TOTAL | 7,75 | 6,49 | 6,58 | 15% after 60 days |
| HDL | 1,15 | 1,00 | 1,06 | |
| LDL | 6,05 | 4,89 | 5,00 | 17% after 60 days |
| TRIGLY | 1,22 | 1,31 | 1,15 | |
| CHO/HDL | 6,74 | 6,49 | 6,20 | |
| LDL/HDL | 5,3 | 4,9 | 4,7 | |
| IM Case #5 (Med) | | | | |
| CHO TOTAL | 7,06 | 6,74 | 6,59 | 6,7% after 60 days |
| HDL | 1,26 | 1,29 | 1,16 | |
| LDL | 5,08 | 4,70 | 4,56 | 10% after 60 days |
| TRIGLY | 1,59 | 1,65 | 1,92 | |
| CHO/HDL | | | | |
| LDL/HDL | 3,6 | | 3,9 | |
| YC Case #6 (Med) | | | | |
| CHO TOTAL | 7,38 | 7,03 | 7,06 | 4,3% after 60 days |
| HDL | 1,49 | 1,65 | 1,66 | |
| LDL | 5,45 | 4,84 | 4,91 | 11.2% after 30 days |
| TRIGLY | 0,97 | 1,18 | 1,07 | |
| CHO/HDL | | | | |
| LDL/HDL | 3,7 | 2,9 | 3,0 | 19% after 60 days |
| ES Case #7 (Med) | | | | |
| CHO TOTAL | 6,33 | 6,11 | 6,16 | 2,7% after 60 days |
| HDL | 1,26 | 1,04 | 1,08 | |
| LDL | 4,24 | 4,24 | 4,48 | |
| TRIGLY | 1,83 | 1,83 | 1,31 | 28,4% after 60 days |
| CHO/HDL | | | | |
| LDL/HDL | 3,4 | 4,1 | 4,2 | |
| RL Case #8 (Med) | | | | |
| CHO TOTAL | 6,41 | 6,64 | 6,84 | 6,7% after 60 days |
| HDL | 1,28 | 1,30 | 1,13 | |
| LDL | 4,73 | 4,85 | 5,02 | |
| TRIGLY | 0,88 | 1,07 | 1,52 | |
| CHO/HDL | | | | |
| LDL/HDL | 3,7 | 3,7 | 4,4 | |

-continued

BIOK + CHOLESTEROL STUDY

| | T = 0 | T = 30 | T = 60 | T = 120 | REDUCTION |
|---|---|---|---|---|---|
| JGT Case #9 (Med) | | | | | |
| CHO TOTAL | 6,33 | 6,36 | | | |
| HDL | 1,88 | 1,90 | | | |
| LDL | 4,07 | 3,93 | | | |
| TRIGLY | 0,84 | 1,16 | | | |
| CHO/HDL | | | | | |
| LDL/HDL | 2,2 | 2,1 | | | TB |
| CC Case #10 (Med) | | | | | |
| CHO TOTAL | 7,64 | | 6,99 | | |
| HDL | 0,96 | | 1,03 | | |
| LDL | 5,18 | | 5,10 | | |
| TRIGLY | 3,31 | | 1,89 | | 43% after 60 days |
| CHO/HDL | 7,9 | | 6,8 | | |
| LDL/HDL | 5,4 | | 5,0 | | |
| XB Case #11 (Med) | | | | | |
| CHO TOTAL | 7,03 | 6,31 | | | 10% after 30 days |
| HDL | 1,23 | 1,18 | | | |
| LDL | 4,97 | 4,45 | | | 10,5% after 30 days |
| TRIGLY | | | | | |
| CHO/HDL | 5,7 | 5,3 | | | |
| LDL/HDL | 4,04 | 3,77 | | | Return to normal |
| XX Case #12 (Med) | | | | | |
| CHO TOTAL | 6,84 | 6,25 | 6,03 | | 12% after 60 days |
| HDL | 1,21 | 1,17 | 1,13 | | |
| LDL | 4,93 | 4,38 | 4,44 | | 9% after 60 days |
| TRIGLY | | | | | |
| CHO/HDL | | | | | |
| LDL/HDL | 4,07 | 3,74 | 3,93 | | |
| CV Case #13 (MR) | | | | | |
| CHO TOTAL | 6,60 | | | 5,18 | 21% after 4 months |
| HDL | 1,28 | | | 1,30 | |
| LDL | 3,51 | | | 2,79 | 20,5% NORMAL |
| TRIGLY | 3,96 | | | 2,39 | 39% |
| CHO/HDL | 5,12 | | | 3,98 | 22% return to NORMAL |
| LDL/HDL | 2,74 | | | 2,14 | 22% return to NORMAL |
| ITC Case #14 (HCLM) | | | | | |
| CHO TOTAL | 9,41 | 8,34 | 7,76 | | 17,5% |
| HDL | 1,27 | 1,11 | 1,10 | | |
| LDL | 7,35 | 6,31 | 5,89 | | 20% |
| TRIGLY | 2,13 | 2,48 | 1,68 | | 21% return to NORMAL |
| CHO/HDL | 7,4 | 7,5 | 7,05 | | |
| LDL/HDL | 5,78 | 5,68 | 5,4 | | |

HCLM - Charles Le Moine Hospital
MED - Medicis
REFERENCES
CHO TOTAL 4,2-5,
HDL 0-0,9
LDL <3,4
TRIGLY 0,4-2,1
CHO/HDL 3,2-4,4
LDL/HDL <3,8 for > 30 years old.

What is claimed is:

1. A biologically pure culture of a microorganism having all of the identifying characteristics of *Lactobacillus acidophilus* CNCM I-1492.

2. A lactic ferment composition comprising the microorganism of claim 1.

3. The lactic ferment composition of claim 2, further comprising at least one other *Lactobacillus acidophilus* strain and at least one *Lactobacillus casei* strain.

4. A method for producing a fermented dairy product comprising the step of fermenting the lactic ferment composition of claim 3 in a milk-based medium by a multi-step fermentation.

5. A fermented dairy product obtained by the method of claim 4, wherein the fermented dairy product comprises at least 500 millions per gram of microorganisms of the *Lactobacillus acidophilus* species, wherein at least 380 million per gram are microorganisms identified as *Lactobacillus acidophilus* CNCM I-1492.

* * * * *